(12) United States Patent
Martin et al.

(10) Patent No.: US 8,747,468 B2
(45) Date of Patent: Jun. 10, 2014

(54) COATINGS FOR THE MANUFACTURE AND APPLICATION OF POLYHYDROXYALKANOATE MEDICAL DEVICES

(75) Inventors: David P. Martin, Arlington, MA (US); Said Rizk, Salem, NH (US); Jon I. Moncrieff, Boston, MA (US); Dennis W. Connelly, Arlington, MA (US)

(73) Assignee: Tepha, Inc., Lexington, MA (US)

( * ) Notice: Subject to any disclaimer, the term of this patent is extended or adjusted under 35 U.S.C. 154(b) by 237 days.

(21) Appl. No.: 13/070,211

(22) Filed: Mar. 23, 2011

(65) Prior Publication Data

US 2012/0053689 A1    Mar. 1, 2012

Related U.S. Application Data

(60) Provisional application No. 61/318,014, filed on Mar. 26, 2010, provisional application No. 61/325,686, filed on Apr. 19, 2010, provisional application No. 61/363,543, filed on Jul. 12, 2010, provisional application No. 61/411,629, filed on Nov. 9, 2010.

(51) Int. Cl.
*A61F 2/12* (2006.01)
*D03D 15/00* (2006.01)
*B29C 47/00* (2006.01)

(52) U.S. Cl.
USPC ............... 623/13.11; 623/13.18; 623/13.2; 57/7; 57/243

(58) Field of Classification Search
CPC ........... A61F 2/12; D03D 15/00; B29C 47/00
USPC ................. 623/1.49–1.54, 8, 13.11–13.2, 623/14.11–15.12; 57/5–7, 243; 139/420 A, 139/426 R, 426 TW; 606/228–231; 28/169
See application file for complete search history.

(56) References Cited

U.S. PATENT DOCUMENTS

| | | | |
|---|---|---|---|
| 5,108,424 A | 4/1992 | Hoffman, Jr. | |
| 5,811,272 A | 9/1998 | Snell | |
| 6,245,537 B1 | 6/2001 | Williams | |
| 6,316,262 B1 | 11/2001 | Huisman | |
| 6,323,010 B1 | 11/2001 | Skraly | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Martin | |
| 6,905,987 B2 | 6/2005 | Noda | |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,476,249 B2 | 1/2009 | Frank | |
| 7,670,372 B2 | 3/2010 | Shfaram | |
| 2002/0132960 A1* | 9/2002 | Haile et al. ................. 528/272 |
| 2003/0211131 A1 | 11/2003 | Martin | |
| 2004/0048065 A1 | 3/2004 | Jen | |
| 2004/0111116 A1 | 6/2004 | Kennedy | |
| 2005/0176326 A1* | 8/2005 | Bond et al. ................. 442/335 |
| 2007/0196423 A1* | 8/2007 | Ruane et al. ............... 424/423 |
| 2007/0198087 A1* | 8/2007 | Coleman et al. .......... 623/13.18 |
| 2008/0082113 A1 | 4/2008 | Bishop | |
| 2009/0082864 A1 | 3/2009 | Chen | |
| 2009/0248071 A1 | 10/2009 | Saint | |
| 2010/0137679 A1 | 6/2010 | Lashinski | |

FOREIGN PATENT DOCUMENTS

| | | |
|---|---|---|
| WO | 9932536 | 7/1999 |
| WO | 0056376 | 9/2000 |
| WO | 2004101002 | 11/2004 |
| WO | 2006015276 | 2/2006 |
| WO | 2007092464 | 8/2007 |

OTHER PUBLICATIONS

Fedorov, et al., "Structure and strength properties of surgical sutures modified with a polyhydroxybutyrate coating", Fibre Chem, 38(6):471-5 (2006).
Hori, et al., "Chemical synthesis of high molecular weight poly(3-hydroxybutyrate-co-4-hydroxybutyrate)", Polymer 36:4703-4705 (1995).
Martin, D., et al., "Medical Applications of Poly-4-hydroxybutyrate: A Strong Flexible Absorbable Biomaterial", Biochem. Eng. J., 16:97-105 (2003).
Steinbüchel, et al., "Diversity of Bacterial Polyhydroxyalkanoic Acids", FEMS Microbiol. Lett. 128:219-228 (1995).
Williams, et al., "Applications of PHAs in Medicine and Pharmacy, in Biopolymers", Polyesters, III, 4:91-127 (2002).

* cited by examiner

Primary Examiner — David Isabella
Assistant Examiner — Yashita Sharma
(74) Attorney, Agent, or Firm — Pabst Patent Group LLP

(57) ABSTRACT

Biocompatible coatings and spin finishes that can be applied to polyhydroxyalkanoate (PHA) polymers, and medical devices made from PHA polymers, have been developed. The coatings impart good lubricity to PHA polymers, particularly to fibers and braids made from these materials, making the coatings ideal for use on medical devices such as PHA braided sutures. The spin finishes can be applied to PHA fibers to facilitate their manufacture, and also for their conversion to other products, including medical textiles. The spin finishes serve to protect multifilament fiber bundles, and keep them intact following extrusion, and also to impart lubricity to the fiber bundles and monofilament fibers so that they are not damaged in subsequent processing steps particularly in textile processing. The coating reduces tissue drag of, for example, braided sutures.

29 Claims, No Drawings

COATINGS FOR THE MANUFACTURE AND APPLICATION OF POLYHYDROXYALKANOATE MEDICAL DEVICES

CROSS REFERENCE TO RELATED APPLICATIONS

This application claims benefit of U.S. Provisional Application No. 61/318,014, filed on Mar. 26, 2010; U.S. Provisional Application No. 61/325,686, filed on Apr. 19, 2010; U.S. Provisional Application No. 61/363,543, filed on Jul. 12, 2010; and U.S. Provisional Application No. 61/411,629, filed on Nov. 9, 2010, all of which are hereby incorporated herein by reference in their entirety.

FIELD OF THE INVENTION

The present invention generally relates to polymeric compositions that can be processed into fibers, and subsequently converted into textile constructs such as knitted and woven meshes, braids, and vascular grafts using continuous processes. The polymeric compositions include coated polyhydroxyalkanoate polymers and copolymers.

BACKGROUND OF THE INVENTION

There is a need for absorbable braided sutures with improved performance. In particular, these sutures should have high initial tensile strength, prolonged strength retention in vivo, good knot security and tie down (with a small knot bundle), good handling characteristics, and be biocompatible. The braided sutures should also have a low tissue drag that minimizes trauma to the sutured tissues. Biocompatible braided polyhydroxyalkanoate ("PHA") sutures, or those having a braided component, can be made with high tensile strength, prolonged strength retention in vivo, and good knot security; however, it would be advantageous if the tissue drag resulting from the braided structure of the suture could be reduced.

A number of different types of coatings have been applied to braided sutures to lower tissue drag. These coatings must: impart good lubricity to the fiber/braid, have a reasonable shelf life, be biocompatible, and be compatible with the physical and chemical structure of the fiber. For example, the coating must not react with the suture fiber, dissolve the fiber, or adversely alter the mechanical and thermal properties of the fiber. Thus, it is desirable to identify coatings that can be applied to PHA braided sutures to reduce tissue drag by imparting good lubricity to the braid and fill the braid interstices without adversely altering the inherent properties of the fiber/braid. Moreover, it is particularly desirable to identify coatings that can be applied to braided sutures, or sutures containing braided components, made from P4HB polymers and copolymers thereof.

In addition to providing coatings for PHA fibers that reduce tissue drag, it is desirable to identify spin finishes that can be applied to PHA fibers to facilitate their manufacture and, optionally, their conversion to other products, including medical textiles. Spin finishes are applied during extrusion of multifilaments to keep the fiber bundle protected and intact, and to impart lubricity to the fiber bundle so that it may be manipulated in subsequent processing steps without damaging the fiber. Spin finishes are also applied to monofilament to facilitate textile processing without damaging the fiber. Spin finishes for medical applications must satisfy a number of conditions. These include compatibility with the fiber (similar to that described for suture coatings), and effectiveness under the process conditions, for example, in processes such as spinning and orienting of the fiber, and in knitting or weaving of the fiber. In addition, it must be easy to apply the spin finish, and easy to remove the spin finish without damaging the fiber or adversely impacting any component in the fiber such as dye, using conditions that are compatible with the fiber's subsequent use in a medical device. Residues of the spin finish should also be easily detectable, and any spin finish left on the device, even residues, needs to be biocompatible. The spin finish should also be stable with a long shelf life, and any spin finish left on the final product should not adversely impact the properties or the shelf life of the final product.

It is also desirable to provide multifilament with a lower denier per filament (dpf) and improved tenacity compared to uncoated multifilament. Such fibers can be used to prepare higher strength medical devices as well as reduce the device profile.

It is an object of the present invention to provide methods to produce coated PHA braids for use as sutures and in other medical devices, wherein the coating provides the device with good lubricity to minimize trauma to tissues, and good knot strength (in the case of a suture), without adversely impacting the properties of the PHA polymer.

It is a further object of the present invention to provide processes to produce PHA multifilament fiber using spin finish, and process PHA monofilament and multifilament fibers into other forms, such as textiles, with the aid of spin finish such that the fibers may be processed without damage, and the spin finish imparts lubricity to aid in the subsequent processing of the fiber.

It is another object of the present invention to provide coated PHA multifilament and monofilament fibers, coated PHA braided sutures, coated PHA braided structures as components of other devices, and other coated PHA medical devices and textiles, including monofilament and multifilament knitted and woven meshes, and vascular grafts, which are biocompatible and can be used in medical applications, for example, as implants for soft tissue repair and reconstruction, temporary wound support, cosmetic, breast, facial, and plastic surgery, and for the regeneration and replacement of tissues. Such devices and textiles may be further coated or encapsulated by or contain collagen.

It is yet another object of the invention to provide PHA multifilament fibers with low filament denier and higher tenacity.

It is still another object of the invention to provide coatings and spin finishes that can be used in processing PHA polymers to yield materials with excellent physical and mechanical properties, and biocompatibility.

SUMMARY OF THE INVENTION

Biocompatible coatings and spin finishes that can be applied to polyhydroxyalkanoate (PHA) polymers, and medical devices made from PHA polymers, have been developed. The spin finishes can be applied to PHA fibers to facilitate their manufacture, and also for their conversion to other products, including medical textiles. The spin finishes protect the multifilament fiber bundles, keeping them intact following extrusion, and imparting lubricity to the fiber bundles and monofilament fibers so that they are not damaged in subsequent processing steps, particularly in textile processing. In the preferred embodiment, the coatings and spin finish are applied to a polyhydroxyalkanoate polymer, and in the most preferred embodiment, the PHA polymer comprises 4-hydroxybutyrate. In a preferred embodiment, the coating or spin finish is a polymer or oligomer of an alkylene oxide, such as ethylene oxide or propylene oxide, or a copolymer thereof.

The spin finish is preferably a liquid at the fiber processing temperature. For example, if P4HB is processed at or near room temperature, the spin finish is preferably a liquid at room temperature. In other embodiments, the polyalkylene oxides can be wetted with water or solvent to provide a liquid solution at the processing temperature. A particularly preferred embodiment is where the spin finish is polyethylene glycol (PEG) with an average molecular weight of approximately 400 Daltons (PEG 400) to 2000 daltons (PEG 2000) applied to a poly-4-hydroxybutyrate polymer or copolymer thereof. PEG with an average molecular weight of approximately 400 Daltons (PEG 400) to 1000 daltons (PEG 1000) is preferred for PHAs being processed at or near room temperature. Higher molecular weights can be preferable for PHAs being processed at higher temperatures.

In another preferred embodiment for the processing of monofilament PHA fibers into textiles, the spin finish is polyethylene glycol sorbitan monolaurate (e.g., a polysorbate detergent available under the brand Tween® 20). A particularly preferred embodiment is where the spin finish, Tween® 20, is applied to monofilament PHA fiber and knitted or woven into a textile construct, and the PHA fiber comprises 4-hydroxybutyrate.

The preferred coating weight for a spin finish will depend on the fiber being processed. Monofilaments require less spin finish than multifilaments, due to the smaller total surface area of a monofilament fiber. So a preferred coating weight on a monofilament may be less than 2 wt %, preferably less than 1 wt %, while for multifilament it may be less than 10 wt %, preferably less than 8 wt %. Spin finishes can be removed by a scouring process to prevent cytotoxicity. In preferred embodiments, the residual content of Tween® 20 after scouring is less than about 0.5 wt %, including less than about 0.4, 0.3, 0.2, 0.1, 0.09, 0.08, 0.07, 0.06, 0.05, 0.04, or 0.03 wt %. In preferred embodiments, the residual content of PEG 400 after scouring is less than about 2 wt %, including less than about 1, 0.5, 0.4, 0.3, 0.2, or 0.1 wt %.

The textile construct produced from the coated PHA fibers may be further coated, impregnated, covered, or encapsulated by or contain collagen.

The coatings impart good lubricity to PHA polymers, particularly to fibers and braids made from these materials, making the coatings ideal for use on medical devices such as PHA braided sutures. Braided monofilament fibers or multifilament yarns are provided that are coated with polymers or oligomers of ethylene oxide, polymers or oligomers of propylene oxide, polyvinyl alcohol, or combinations thereof. These braided fibers or yarns have an average tissue drag force at least 10% lower than the uncoated braid, including at least 20, 30, 40, 50, 60, 70, 80, 90, 100% lower than the uncoated braid.

The polyhydroxyalkanoate of the braided fiber or yarn preferably has a molecular weight between 50,000 and 1,200,000. In preferred embodiments, the polyhydroxyalkanoate is 4-hydroxybutyrate.

In a preferred embodiment, the coating is polyethylene glycol (PEG) with an average molecular weight of approximately 1000 Daltons (PEG 1000) to 10,000 daltons (PEG 10000) applied to devices, such as braided sutures, derived from poly-4-hydroxybutyrate or copolymers thereof.

In another embodiment, the coating is polyvinyl alcohol (PVOH). A particularly preferred embodiment is where the coating is polyvinyl alcohol applied to a poly-4-hydroxybutyrate polymer or copolymer thereof or applied to devices, such as braided sutures, derived from poly-4-hydroxybutyrate or copolymers thereof.

In preferred embodiments, the biocompatible coating is present on the PHA polymers or the medical devices made from PHA polymers in a coating weight of about 0.1 wt % to 10 wt %, including about 0.1, 0.2, 0.3, 0.4, 0.5, 0.6, 0.7, 0.8, 0.9, 1, 2, 3, 4, 5, 6, 7, 8, 9, and 10 wt %. For example, PEG2000 is preferably present on the PHA polymers or the medical devices made from PHA polymers in a coating weight of less than 10 wt %, more preferably less than 7 wt %, even more preferably less than 5 wt %. For example, PVA is preferably present on the PHA polymers or the medical devices made from PHA polymers in a coating weight of less than 6 wt %, more preferably less than 4 wt %, even more preferably less than 3 wt %.

A method of reducing the tissue drag force of a braided suture formed from polyhydroxyalkanoate filaments is also provided. This method can involve coating the braided suture with polymers or oligomers of ethylene oxide, polymers or oligomers of propylene oxide, polyvinyl alcohol, or combinations thereof.

DETAILED DESCRIPTION OF THE INVENTION

I. Definitions

"Polyhydroxyalkanoates" or "PHAs" are linear polyesters produced in nature by bacterial fermentation of sugar or lipids. Depending upon the microorganism and the cultivation conditions, homo- or copolyesters with different hydroxyalkanic acids are generated.

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Lexington, Mass.).

"Copolymers of poly-4-hydroxybutyrate" as generally used herein means any polymer comprising 4-hydroxybutyrate with one or more different hydroxyalkanic acid units.

"Blend" as generally used herein means a physical combination of different polymers, as opposed to a copolymer comprised of two or more different monomers.

"Breast reconstruction devices" means devices for (i) breast augmentation, including devices for use with breast implants (e.g. saline or silicone implants), (ii) mastopexy, (iii) breast reduction (including removal, reshaping and reorienting of breast tissue), and (iv) breast reconstruction following mastectomy with or without breast implants.

"Tensile modulus" is the ratio of stress to strain for a given material within its proportional limit.

"Toughness" means a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993)

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993).

"Molecular weight" as used herein, unless otherwise specified, refers to the weight average molecular weight (Mw), not number average molecular weight (Mn), and is measured by gel permeation chromatography (GPC) relative to polystyrene.

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

"Cytotoxicity" refers to the harmful affect of a medical device on cells as set forth in ISO 10993-5. Cytotoxicity can be measured using a rapid, standardized test that is very sensitive and inexpensive. These tests can determine if the materials in a medical device contain significant quantities of harmful extractables that negatively effect cellular components. Testing is required for all types of medical devices. An agar overlay media can be placed on top of a monolayer of L-929 cells, and a sample is placed on top of the agar media, then incubated. For MEM elution, an extract of the sample in Minimum Essential Medium (MEM) is placed in contact with the monolayer of L-929 cells and then incubated. In both methods the cells are scored for cytotoxic effect.

"Spin finishes" are lubricants and antistatic agents that are applied to textile fibers and yarns during production and processing.

"Denier" is a unit of weight of fiber or yarn. The weight in grams of 9,000 meters of fiber or yarn is its denier.

"Tenacity" is the strength of a yarn or fiber for its given size. It may be defined as the grams of breaking force per denier or breaking strength (grams force) divided by denier (i.e. grams per denier, or gpd).

"Pick count" is defined as the number of crossovers of sheath yarns per linear inch of suture or braid.

"PPI" stands for picks per inch.

"TPI" stands for twists per inch.

"Lubricity" is the measure of the reduction in friction by a lubricant. Lubricity of a material cannot be directly measured, so tests are performed to quantify a lubricant's performance. This is done by determining how much wear is caused to a surface by a given friction-inducing object in a given amount of time. For sutures, lubricity can be determined by measuring tissue drag. A monofilament has low tissue drag, meaning it passes smoothly through tissue. Braided or twisted sutures have higher tissue drag, but are easier to knot and have greater knot strength. Braided sutures can be coated to increase lubricity and lower tissue drag.

II. Compositions

Methods have been developed to produce lubricious compositions of PHA polymers that are suitable for the manufacture of PHA fibers and yarns, and for the manufacture of medical devices and medical device components, as well as to improve the lubricity of certain medical devices, such as sutures comprising PHA braided structures Multifilament yarn comprising polyhydroxyalkanoate polymer has a denier per filament of less than 4.0. The multifilament yarn has a tenacity greater than 6.1 grams per denier. These methods have been applied to P4HB multifilaments prepared by melt processing, and to P4HB multifilaments and monofilaments braided, woven or knitted into medical device products, such as braided sutures and surgical meshes.

A. Polymers

The processes described herein can typically be used to apply coatings or spin finishes to polyhydroxyalkanoate polymers, and more preferably to poly-4-hydroxybutyrate (P4HB) or a copolymer thereof. Copolymers include P4HB with 3-hydroxybutyrate, and P4HB with glycolic acid monomer. P4HB and copolymers thereof can be obtained from Tepha, Inc. of Lexington, Mass. Preferred PHA polymers have a weight average molecular weight (Mw) suitable for melt processing, and more preferably a Mw of 50,000 to 1,200,000, and even more preferably 100,000 to 800,000 based on gel permeation chromatography (GPC) relative to polystyrene standards. If desired, the PHA polymer may be blended with another PHA polymer prior to melt extrusion of the fibers, or blended with a non-PHA material, including other absorbable biocompatible polymers, dyes and active agents (such as drug molecules or other therapeutic, prophylactic or diagnostic agents).

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure

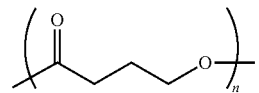

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production. Several biosynthetic routes are currently known to produce P4HB:

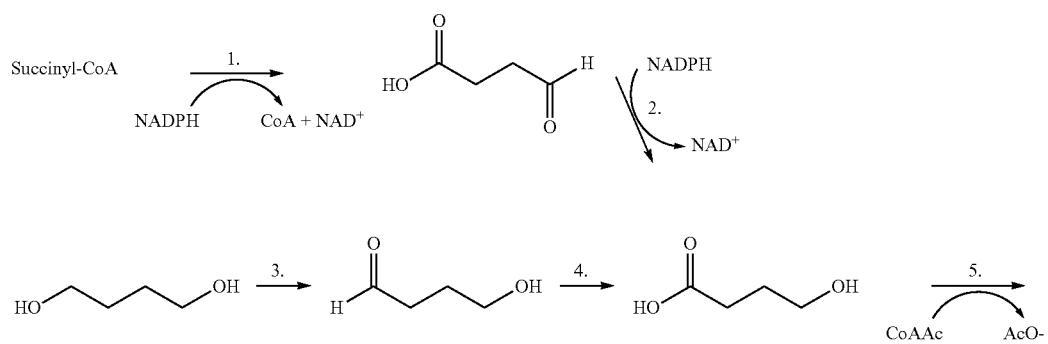

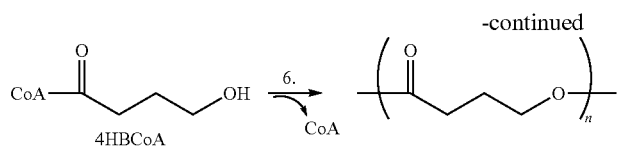

This schematic shows some of the known biosynthetic pathways for the production of P4HB. Pathway enzymes are: 1. Succinic semialdehyde dehydrogenase, 2. 4-hydroxybutyrate dehydrogenase, 3. diol oxidoreductase, 4. aldehyde dehydrogenase, 5. Coenzyme A transferase and 6. PHA synthetase.

Chemical synthesis of P4HB has been attempted, but it has been impossible to produce the polymer with a sufficiently high molecular weight that is necessary for most applications (Hori, Y., et al., *Polymer* 36:4703-4705 (1995)).

U.S. Pat. Nos. 6,245,537, 6,623,748 and 7,244,442 describe methods of making PHAs with little endotoxin, which is suitable for medical applications. U.S. Pat. Nos. 6,548,569, 6,838,493, 6,867,247, 7,268,205, and 7,179,883 describe use of PHAs to make medical devices. Copolymers of P4HB include 4-hydroxybutyrate copolymerized with 3-hydroxybutyrate or glycolic acid (U.S. patent application No. 20030211131 by Martin and Skraly, U.S. Pat. No. 6,316,262 to Huisman, et al., and U.S. Pat. No. 6,323,010 to Skraly, et al.). Methods to control molecular weight of PHA polymers have been disclosed by U.S. Pat. No. 5,811,272 to Snell, et al.

PHAs with controlled degradation and degradation in vivo of less than one year are disclosed in U.S. Pat. Nos. 6,548,569, 6,610,764, 6,828,357, 6,867,248, and 6,878,758 to Williams, et al. and WO 99/32536 to Martin, et al. Applications of P4HB have been reviewed in Williams, S. F., et al., *Polyesters, III,* 4:91-127 (2002), and by Martin, D., et al. Medical Applications of Poly-4-hydroxybutyrate: A Strong Flexible Absorbable Biomaterial, *Biochem. Eng. J.* 16:97-105 (2003). The latter reference also describes monofilament fibers and textiles of P4HB. Medical devices and applications of P4HB have also been disclosed by WO 00/56376 to Williams, et al. Several patents including U.S. Pat. Nos. 6,555,123, 6,585,994, and 7,025,980 to Williams, et al. describe the use of PHAs in tissue repair and engineering.

WO 04/101002 to Martin, et al. discloses monofilament and multifilament fibers, and knitted meshes of P4HB produced by knitting these fibers.

WO 06/015276 to Rizk, et al. discloses non-curling P4HB fibers for use as sutures, and other medical devices including surgical meshes.

WO 07/003,185 to Coleman, et al. discloses interposition and augmentation devices for tendon and ligament repair comprising P4HB fibers, and P4HB multifilament fiber with a filament denier of 4.4 and tenacity of 6.04 gram/denier.

B. Coatings and Spin Finishes

The processes described herein typically use polymers or oligomers of ethylene oxide or propylene oxide as the spin finish and coating materials. The coating material can also be, for example, polyvinyl alcohol. For the textile processing of PHA monofilament fibers, the spin finish may be Tween® 20, a polyoxyethylene derivative of sorbitan monolaurate.

Preferred polymers or oligomers of ethylene oxide and propylene oxide for textile processing have relatively low molecular weights, low toxicity, good solubility in water and alcohols, can be easily detected, can be easily removed from the PHA polymer preferably using water, and can be formulated so that they can be readily applied to PHA polymers preferably by an application process that employs a pump. The preferred polymers or oligomers of ethylene oxide and propylene oxide should also be compatible (non-absorbable and non-reactive) with the PHA polymers, as well as impart and maintain lubricity to the PHA polymer. The spin finish and coatings should not readily leave the PHA polymer surface during processing unless in a scouring process specifically designed to remove them.

A preferred polymer of ethylene oxide is polyethylene glycol having an average molecular weight of approximately 400 to 10,000 daltons (e.g., PEG 400, PEG 2000, and PEG 10000), most preferably 1000 to 10,000, depending on whether the polymer is being used as a spin finish for textile processing or a coating to reduce tissue drag of a device, such as a suture. PEG 400 passed cytotoxicity testing at a coating weight of 4.8 wt %. Polyethylene glycols manufactured by Spectrum Chemical Manufacturing Corporation are available under the tradename CARBOWAX. In addition, blends of the above-mentioned polymers and oligomers can be used as spin finish and coating materials.

Polyvinyl alcohol ("PVA") can also be used as a coating. Preferred coating weights for PVA range from 0.1 to 6%, preferably less than 3 wt %.

C. Other Components

The PHA polymers and copolymers may contain other materials, including plasticizers, nucleants, other polymers (including absorbable polymers), additives, dyes, and compatibilizers. Examples of plasticizers are disclosed by U.S. Pat. No. 6,905,987 to Noda et al. Other components may be added to impart benefits such as, but not limited to, increased stability, including oxidative stability, brightness, color, flexibility, resiliency, workability, processibility (by addition of processing aids), and viscosity modifiers. Other absorbable polymers that may be included in the compositions include those comprising the following monomers: glycolic acid, lactic acid, trimethylene carbonate, p-dioxanone, and caprolactone.

Active components, including therapeutic, diagnostic and/or prophylactic agents, or other substances may be incorporated into the PHA polymers and copolymers, either at the time of extrusion, or in a later processing step, particularly as a coating. Such compositions may be used for controlled release of the drugs or other substances. These may be proteins, peptides, sugars, polysaccharides, glycoproteins, lipids, lipoproteins, nucleic acid molecules, inorganic or organic synthetic molecules, or combinations thereof. It may also be advantageous to incorporate contrast agents, radiopaque markers, or radioactive substances.

A particularly preferred coating is collagen, which exhibits excellent cell adhesion properties, promotes natural wound healing, and stimulates fibroblast adhesion and growth. In particular, collagen coated on PHA fabrics can promote incorporation of the device into tissue structures, and therefore it can be particularly desirable to apply collagen to the surfaces of PHA devices and even to entirely cover or encapsulate the device with collagen.

For certain applications it may also be desirable to incorporate fillers, including materials such as, but not limited to, titanium dioxide, calcium carbonate, hydroxyapatite, and tricalcium phosphate.

III. PHA Medical Devices and Methods of Manufacturing

A. Fibers and Textiles for Making PHA Medical Devices

In a preferred embodiment, PHA multifilament can be prepared with a denier per filament (dpf) of less than 4, and even more preferably less than 3 dpf. It has been discovered that P4HB multifilament can be prepared with a dpf of approximately 2. It has also been discovered that P4HB multifilament can be prepared with a tenacity of greater than 6.5. Application of polymers and oligomers of ethylene and propylene oxide to the multifilament extrudate protects the extruded fiber bundle, and keeps the fiber bundle intact so that the individual fibers are not separated and damaged. The spin coating remains stable on the P4HB multifilament even as the yarn is moving. It has also been discovered that polymers and oligomers of ethylene or propylene oxide impart good lubricity to the PHA polymers, and can be pumped during the manufacture of the fibers under the conditions required for extrusion of the multifilament. In an even more preferred embodiment, P4HB multifilament fibers are coated with PEG400.

Polymers and oligomers of ethylene or propylene oxide may also be applied to other fibers of PHA polymers and copolymers to aid in subsequent processing. In a preferred embodiment, polymers and oligomers of ethylene oxide are applied to P4HB monofilament fibers. In an even more preferred embodiment, PEG400 is applied to P4HB monofilament fibers prior to further processing.

In addition to using polymers or oligomers of ethylene or propylene oxide to process PHA monofilament into textile products, such as surgical meshes, it has been discovered that Tween® 20 may also be used for this purpose. In a preferred embodiment, Tween® 20 is applied to P4HB monofilament fibers prior to further processing.

It has been found that PHA polymers and copolymers coated with polymers and oligomers of ethylene or propylene oxide can be readily converted into medical device products, particularly products containing textiles such as braided sutures, monofilament and multifilament meshes, small tubes (including vascular grafts), and other knitted and woven devices. Use of polymers and oligomers of ethylene or propylene oxide as spin finishes minimize damage to the fibers during processing. In contrast, PHA fibers processed without spin finish can be severely damaged in subsequent processing steps.

It has also been found that polymers and oligomers of ethylene oxide can be left on the PHA polymers without adversely altering the properties of the polymer and the device. Long term exposure to these spin finishes/coatings does not significantly alter the mechanical properties or molecular weight (Mw) of the fibers. This is important particularly if there is a significant time period between, for example, the manufacture of the multifilament and its subsequent processing into a textile construct.

It has also been discovered that Tween® 20 can be used as a spin finish on PHA monofilament fibers that are used to produce medical device products, particularly those produced by knitting and weaving processes (such as monofilament surgical mesh devices). Use of Tween® 20 on monofilament PHA fibers as a spin finish minimizes damage to the fibers during processing.

In most cases it is necessary to remove substantially all the spin finish from a medical device prior to its use. Spin finishes have a tendency to attract particulate to the surface they adhere to, and therefore removal of the spin finish is desirable in most instances. High levels of certain spin finishes can also be too toxic for medical device use, and in these cases removal to a non-toxic level is essential (otherwise the spin finish cannot be used). It should be noted that some PHA polymers, including P4HB polymers and copolymers thereof, have relatively low melting points that significantly limit conditions under which spin finishes can be applied and removed. For example, exposure to high temperatures will melt the PHA fibers or cause changes in the physical (e.g. mechanical and morphological) properties of the polymers. Thus, spin finishes that are applied or removed at high temperatures cannot be used. Furthermore, the PHA polymers are also degradable, and therefore susceptible to hydrolysis under certain conditions, and are soluble in a range of solvents. These PHA properties also limit the choice of available spin finishes (e.g. some solvents used to apply or remove spin finish will dissolve the P4HB). As will be apparent to one skilled in the art, selection of a spin finish for a PHA polymer or copolymer is a complicated task with the spin finish needing to satisfy a large number of performance requirements not just in processing but also in the removal process.

In a preferred embodiment, it has been found that polymers and oligomers of ethylene and propylene oxide can be substantially removed from PHA polymers and copolymers after product fabrication without damaging the properties of the PHA polymers or the PHA fibers, and that the resulting scoured products pass cytotoxicity testing. Notably, certain other spin finishes tested, for example, DacoSpin®, failed cytotoxicity testing under the same conditions with P4HB multifilament braided sutures. In a preferred embodiment, devices of PHA polymers and copolymers treated with polymers and oligomers of ethylene and propylene oxide are scoured with water to remove the spin finish. These devices may also be washed with alcohol as an alternative, or additional, scouring process, to further reduce the level of spin finish remaining on the device. In a particularly preferred embodiment, devices comprising P4HB fibers coated with PEG400 are scoured with water, and optionally rinsed with an alcohol solution.

In another preferred embodiment, it has been found that Tween® 20 can also be applied to PHA monofilament fibers as a spin finish and be substantially removed from PHA polymers and copolymers after product fabrication without damaging the properties of the PHA polymers or the PHA monofilament fibers, and that the resulting scoured products pass cytotoxicity testing.

Fibers derived from PHA polymers and copolymers coated with polymers and oligomers of ethylene and propylene oxide as spin finish, and fibers derived from PHA monofilament coated with Tween® 20 as spin finish, possess properties that are desirable in preparing medical products, particularly implantable medical devices. For example, these fibers may be used to make partially or fully absorbable biocompatible medical devices, or components thereof. Such devices may include, but are not limited to: stent, stent graft, drug delivery device, device for temporary wound or tissue support, device for soft tissue repair, devices for cosmetic, neck and plastic surgery, replacement or regeneration (including facial surgery procedures such as blepharoplasty, facial scar revisions, forehead lifts (brow lifts), mentoplasty, malar augmentation, otoplasty, rhinoplasty, neck lift surgery, threadlifts (to lift and support sagging areas of the face, brow and neck), and rhytidectomy), repair patches including hybrid meshes, tissue engineering scaffolds, retention membranes (for example, to retain bone graft), anti-adhesion membrane, tissue separation membrane, hernia repair device, breast reconstruction device, device coating (including devices to improve fixation), cardiovascular patch, vascular closure device, vascular graft, sling, biocompatible coating, rotator cuff repair device, meniscus repair device, adhesion barrier, guided tissue repair/regeneration device, articular cartilage repair device, nerve guide, tendon repair device, ligament repair device, intracardiac septal defect repair device, including but not limited to atrial septal defect repair devices and PFO closure devices, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

B. Methods of Making PHA Multifilament Yarn Coated with Spin Finish

In a preferred method, bulk PHA resin in pellet form is dried to under 300 ppm of water using a rotary vane vacuum pump system. The dried resin is transferred to a feed hopper with a nitrogen purge to keep the pellets dry. The pellets are gravity fed into a chilled feeder section, and introduced into an extruder barrel, for example, 0.75 inches in diameter and 25.69 inches long via an extrusion screw with 30:1 L/D ratio. A preferred extruder barrel contains four heating or extrusion zones and is manufactured by American Kuhne. The heated and softened resin from the extruder is fed into a heated metering pump (melt pump) and from the melt pump the extruded resin is fed into the heated block. The spin head houses a spin pack comprising filtering media (screens) and spinnerets containing the desired number of holes for forming the individual filaments of the yarn. (For example, 15, 30 and 60 or more holes.) The extruded filaments exit the spinneret, pass through a hot chimney, and are then air-cooled until they solidify inside a contained, clear tube. The resulting yarn is then passed through a spin finish applicator, over two rotating godets, and is collected on a precision winder as the yarn exits the second godet. The denier of the yarn at this point can range significantly depending on the number of holes and speed of the godets. A preferred range is 120-840 denier. The quantity of spin finish applied to the filaments during passage through the spin finish applicator may be controlled by varying the concentration of the spin finish while keeping all other parameters constant. This also allows direct comparison between spin finishes. In a preferred method, orientation of the yarn is accomplished offline, although it can also be done inline. In a preferred method, the extrudate is collected onto spools and then three sets of paired godets are used to orient the yarn from a payoff system holding the extrudate collection spool. The extruded yarn is rewet via a controlled pump speed spin finish applicator. In a preferred method, the yarn is hot stretched.

In another preferred method, the PHA multifilament has a denier per filament of less than 4, and more preferably less than 3.

In a particularly preferred method, the PHA polymer is P4HB with a weight average molecular weight of 100,000-800,000, and the spin finish is PEG400.

C. Method of Making Braided PHA Multifilament Sutures

In a preferred method, drawn 60-filament yarn coated with spin finish is formed into braided sutures as follows. PHA yarn is twisted and/or plied and wound onto bobbins. These bobbins are then placed on 8, 12 or 16-carrier braiders and braided at various picks per inch. For some constructions, cores are made and put in the center of the braid, for example, 60-filament yarn, multiple plied yarn strands, or monofilament fibers.

In the preferred method, braided sutures are manufactured from yarns comprising 4-hydroxybutyrate that are produced from P4HB polymers and copolymers with a weight average molecular weight between 100,000 and 800,000. The braided sutures have a tenacity from about 3-8 grams per denier, a percent elongation to break of less than 50 percent, and a denier per filament from 0.1 to 8.0. The braids are preferably made from yarns that are oriented to about 1.4 to 3.1 denier per filament (dpf). In one embodiment, yarns comprising 4-hydroxybutyrate can be braided into sutures using conventional or spiroid braid constructions as shown in Table 1.

TABLE 1

| 4-hydroxybutyrate yarns | | | | | |
|---|---|---|---|---|---|
| USP Size | Diam. mm | Approx Denier | USP Size | Diam. mm | Approx Denier |
| 3.0-5.0 | >0.600 | >3600 | 3/0 | 0.20-0.249 | 800 |
| 2.0 | 0.50-0.599 | 3500 | 4/0 | 0.15-0.199 | 600 |
| 1 | 0.40-0.499 | 2500 | 5/0 | 0.10-0.149 | 400 |
| 0 | 0.35-0.399 | 1700 | 6/0 | 0.070-0.099 | 200 |
| 2/0 | 0.30-0.399 | 1200 | 7/0 | 0.050-0.069 | <100 |

D. Scouring of PHA Devices and Fibers to Remove Spin Finish

In a preferred method, spin finish is removed from PHA fibers and devices by scouring with water. The PHA material is washed in a water bath, using cold water—typically between 4° C. and ambient temperature (i.e., water sufficiently cold that it does not adversely alter the properties of the PHA material, such as where the PHA has a low melting temperature). After washing for a pre-determined time, for example, five minutes or more, the PHA material is rinsed with fresh water. In the preferred method, a water-soluble detergent, such as Tween 20 or Tween 80, may also be added to the water at 1 to 10,000 ppm to facilitate scouring of the PHA material, and then the PHA material is carefully rinsed to remove the detergent. Placing the samples in an ultrasonic bath for a predefined period of time, for example, from 1 second up to 24 hours or 48 hours, can also be used to achieve enhanced scouring of the PHA material in water. As an alternative to adding detergent to the water, the PHA materials may also be scoured with aqueous solutions of alcohol, for example, ethanol or isopropylalcohol, and if desired, combining this treatment with ultrasonic cleaning. Alternatively, the PHA fibers and devices may be washed with alcohol solutions after scouring with water. Once the PHA fibers and devices have been scoured, the materials may be allowed to dry at ambient, or more preferably dried under vacuum to remove residual moisture/solvent. It will be apparent to those skilled in the art that various combinations of washing steps can be used to scour the PHA fibers and devices.

E. Method of Coating PHA Devices with Collagen

In a preferred method, devices prepared from PHA polymers, including PHA sutures, meshes, and other textile constructs, are coated with collagen. The coating may range from a thin coating for example on the surface of a PHA fiber to the complete coverage or encapsulation of a PHA device, such as a mesh, by collagen. A particularly preferred method involves completely encapsulating a mesh such that the device is effectively a collagen sponge reinforced with a PHA mesh. Such PHA reinforced collagen sponges or coated devices can have the following desirable properties: good handling characteristics; absorb tissue exudate; prevent, reduce or delay contracture of the wound; improve suture holding; conform well to the wound or surgical site; provide a superior cosmetic repair, prevent leakage; and facilitate tissue in-growth and a strong repair.

In a preferred method, PHA devices, particularly collagen sponges reinforced with PHA fabrics, can be prepared by immersing the PHA device in an acid-swollen collagen suspension that has been blended into a slurry. For example, the monofilament mesh of Example 8, may be coated with collagen in this manner. After immersion, the coated device may be air-dried or freeze-dried, and if necessary the process repeated multiple times to build up the thickness of the coating. In a preferred method, the process is repeated until the entire PHA device is encapsulated in a collagen sponge. Alkali and neutral slurries of collagen may also be used (as well as collagen compositions that have been pre-digested with pepsin to remove the nonhelical terminal regions of the collagen molecule). Generally, freeze drying is preferred when it is desirable to obtain a porous collagen coating or sponge, and porosity can be tailored, for example, by altering the concentration of the collagen in the slurry. In a particularly preferred method, the average porosity of the device is controlled to optimize the invasion of host fibroblasts in vivo, and is at least 5 µm in diameter, and most preferably in the range of 5-150 µm. In a preferred method, the coated device may be pressed, molded or cut to the desired device shape.

In order to improve the adhesion of collagen to the PHA polymer, the PHA polymer may be modified prior to coating with collagen. A preferred method is modification by treatment with plasma. In a particularly preferred plasma treatment, ammonia gas is used to produce a PHA polymer surface rich in amine groups. Plasma modified PHA surfaces may be coated, or crosslinked, and can have an increased affinity to bind collagen.

In certain cases it is desirable to crosslink the collagen after coating of a PHA device. Crosslinking can increase the tensile strength of the device, and improve the integrity of the coating and the handling of the device. Crosslinking can also be used to control the rate of in vivo degradation, and tailor the rate to the application. For example, crosslinking can be used to slow down the degradation of a PHA reinforced collagen sponge in order to allow the implanted collagen to be replaced by host collagen. This can be particularly important where tissue reinforcement or regeneration is necessary, for example, in hernia repair and rotator cuff repair procedures, and where a strong repair is necessary.

A number of methods can be used to crosslink the collagen of a collagen coated PHA device. These include the formation of ionic bonds, covalent bonds, and hydrogen bonds. In a preferred method, the carboxyl groups of aspartic and glutamic residues or the epsilon-amino acid groups of lysine and hydroxylysine are crosslinked. The amino side-chain groups of asparagine and glutamine may also be crosslinked, and less preferably the hydroxyl groups of serine, threonine and hydroxyproline. In a preferred method, the collagen is covalently crosslinked with aldehydes most preferably formaldehyde, glutaraldehyde, glyceraldehyde, glyoxal, acetaldehyde, acrolein, and dialdehyde starch. The collagen may also be crosslinked with reagents such as carbodiimides, acyl azides, and isocyanates (e.g. 1,6-diisocyanatohexane). The degree of crosslinking can be altered, for example, by varying the concentration of crosslinking agent, and reaction time. In another preferred method, the collagen is ionically crosslinked with trivalent metals, preferably chromium or aluminum. In yet another method, the collagen may be crosslinked with borohydrides (e.g. sodium or potassium borohydride). In yet still another method, the collagen may be crosslinked by exposure to UV or other sources of irradiation. In one preferred embodiment, the collagen is crosslinked by UV light at 120 µW/cm$^2$. In a less preferred method, the collagen may be crosslinked by heating preferably under vacuum. In the preferred method, the collagen is crosslinked after coating of the PHA device, however, the collagen may alternatively be crosslinked prior to coating.

The degree of crosslinking may also be controlled by derivatization of the collagen side groups prior to crosslinking, for example, by methylation, acetylation or esterification. This method may also be used to further modify the device properties.

The collagen coated PHA devices may further comprise other materials. These materials may be added to control the device degradation rate, add or enhance other properties. For example, collagen sponges reinforced by PHA meshes can carry active agents such as antibiotics, or other materials such as hyaluronic acid and fibronectin. Such compounds could be used to increase fibroblast proliferation and improve organized tissue repair. A preferred method incorporates up to 5% hyaluronic acid (based on collagen weight). Another preferred method incorporates up to 20% chondroitin sulfate. The latter may enhance cellular attachment. Plasticizers may also be added, for example, to improve flexibility and optimize porosity. Preferred plasticizers are biocompatible and absorbable, and include sorbitol, glycerine, and citrate.

In a preferred method, the collagen may also be further derivatized to alter its biological activity. In a preferred method, heparin is bound to the collagen to create non-thrombogenic surfaces.

The collagen coated PHA devices are preferably sterilized by ethylene oxide or irradiation, most preferably at 2.5 to 10 millirad.

F. Fabrication of PHA Breast Reconstruction Devices

PHA polymers and copolymers possess properties that are desirable for preparing devices for use in breast reconstruction, cosmetic surgery, facial and neck surgery. In a preferred method, PHA fibers are converted into breast reconstruction devices. In a particularly preferred method, PHA fibers are converted into meshes for breast reconstruction. Preferably, these meshes permit some fibrous tissue to grow into and around the mesh to reinforce it, have initial strength and stiffness to provide support, and yet are soft, supple, and barely palpable upon implantation. Importantly, the meshes are sufficiently soft to prevent rippling of the mesh during palpation of the breast. In an even more preferred method, PHA fibers are woven into three-dimensional shapes for use as breast reconstruction devices. Particularly preferred designs are the BREFORM™ internal bra systems used for mastopexy, and manufactured by Aspide Médical, La Talaudiere, France, and sling-shaped devices designed to support the breast or a breast implant, as described for example by U.S. Pat. No. 7,476,249 to Frank, US Patent Application No. 2010/0137679 to Lashinski et al., and U.S. Pat. No. 7,670,372 to Shfaram et al., and the mesh breast implant support device described by US Patent Application No. 2009/0082864 to Chen. The PHA meshes may be derived from PHA monofilament, PHA multifilament, or combinations of these constructs. The mesh devices may also be hybrid structures, for example, comprising PHA fibers and polypropylene and/or polyester fibers. In a further embodiment, the PHA fibers may be used as suspension members and support elements for breast reconstruction as described by US Patent Application No. 2008/0082113 to Bishop, and US Patent Application No. 2009/0248071 to Saint et al.

G. Coating Braided Sutures to Reduce Tissue Drag

Braided or twisted sutures have higher tissue drag (i.e., force required to pull the suture through tissue), but are easier to knot and have greater knot strength. The disclosed coatings impart good lubricity to PHA polymers, particularly to fibers and braids made from these materials, making the coatings ideal for use on medical devices such as PHA braided sutures. Therefore, braided or twisted PHA sutures are preferably coated with polymers or oligomers of ethylene oxide, polymers or oligomers of propylene oxide, polyvinyl alcohol, or combinations thereof. These braided or twisted PHA sutures have an average tissue drag force at least 10% lower than the uncoated braid, including at least 20, 30, 40, 50, 60, 70, 80, 90, 100% lower than the uncoated braid.=

In a preferred embodiment, the coating is polyethylene glycol (PEG) with an average molecular weight of approximately 1000 Daltons (PEG 1000) to 10,000 daltons (PEG 10000). In another embodiment, the coating is polyvinyl alcohol (PVOH). A particularly preferred embodiment is where the coating is polyvinyl alcohol.

In preferred embodiments, the biocompatible coating is present on the twisted or braided PHA sutures in a coating weight of about 0.1 wt % to 10 wt %, including about 0.1, 0.2, 0.3, 0.4, 0.5, 0.6, 0.7, 0.8, 0.9, 1, 2, 3, 4, 5, 6, 7, 8, 9, and 10 wt %. For example, PEG2000 is preferably present on twisted or braided PHA sutures in a coating weight of less than 10 wt %, more preferably less than 7 wt %, even more preferably less than 5 wt %. For example, PVA is preferably present on the twisted or braided PHA sutures in a coating weight of less than 6 wt %, more preferably less than 4 wt %, even more preferably less than 3 wt %.

The present invention will be further understood by reference to the following non-limiting example.

Example 1

Preparation of P4HB Multifilament Coated with Spin Finish

P4HB (Tepha, Inc., Lexington, Mass.) (Mw 200-600K) was extruded into P4HB multifilament as described in Section II.A (Method of Making PHA Multifilament Coated with Spin Finish) using the extruder operating conditions set forth in Table 2, and spinnerets with 15, 30 and 60 holes.

TABLE 2

Extruder Operating Conditions for P4HB Multifilament

| Feed | | | | |
|---|---|---|---|---|
| | 1 | 2 | 3 | 4 |
| 15° C. ± 10° C. | 75° C. ± 40° C. | 180° C. ± 50° C. | 215° C. ± 40° C. | 250° C. ± 40° C. |

| Pump | Block | Spinneret | Chimney | Extruder RPM |
|---|---|---|---|---|
| 230° C. ± 30° C. | 230° C. ± 30° C. | 230° C. ± 30° C. | 110° C. ± 60° C. | 1 ± 1 |

| Take Up | | | Pressure | | Melt |
|---|---|---|---|---|---|
| G1 MPM | G2 MPM | SF RPM | In | Out | Pump RMP |
| 10 ± 10 | 10 ± 11 | 5 ± 5 | 1400 ± 80 | 600 ± 400 | 16 ± 9 |

The P4HB yarn extrudate was oriented offline using 3 sets of paired godets as described in Section II.A using the conditions for orientation set forth in Table 3.

TABLE 3

Orientation Conditions for P4HB Multifilament

| Speed (MPM) | | | Roll Temperature (° C.) | | |
|---|---|---|---|---|---|
| GP 1 | GP 2 | GP 3 | GP 1 | GP 2 | GP 3 |
| 10 | 60 ± 20 | 60 ± 20 | Ambient | 56 ± 10 | 40 ± 10 |

Multiple extrusion runs were undertaken with different spin finishes, and different concentrations of spin finish in order to identify those spin finishes that could be readily applied as a neat spin finish or as a solution in a compatible solvent preferably in liquid form, and would provide good lubricity, protect the fiber bundle and keep it intact, in addition to providing samples for biocompatibility testing, testing in textile manufacturing processes, and in scouring processes. The spin finish or solution thereof would preferably have a viscosity in the range of 1 to 500,000 cP. The following spin finishes were evaluated: Dacospin® (Pulcra Chemicals), Lurol (Goulston Technologies), PEG400 (Spectrum Chemical), PEG40 Stearate, Tween 20 (Uniqema), propylene glycol (Alfa Aesar), Filapan® (Dystar), and Glycerin (PTI Process Chemicals).

A 50% aqueous solution of glycerin was selected and evaluated based on lubricity. However, combination with the P4HB multifilament fiber provided a very sticky product that was too difficult to process, and at higher concentrations resulted in fiber breakage during orientation.

Although the viscosity of Tween® 20 without dilution was found to be too high to allow consistent pumping, concentrations of 10, 25 and 50% in water or ethanol could be applied to the fiber during extrusion, and concentrations of 1% and 10% were applied during orientation. During orientation, Tween® 20 was found to be effective at keeping the fiber bundle intact.

Lurol was successfully applied to the P4HB yarn at concentrations of 10, and 50%, however, the fiber bundle did not stay intact when paying off onto the orientation line, and many broken filaments were observed.

PEG400 was applied to the P4HB yarn at concentrations of 10, 25 and 50%, and at a 1% concentration for orientation. This spin finish displayed ideal properties by providing good lubricity, keeping the fiber bundle intact, and allowing easy payoff during orientation. Visual inspection under a microscope with a 10× magnification confirmed that the lubricant was spread throughout the fiber.

PEG40 Stearate was found to be too viscous at high concentrations, and therefore was evaluated at 10 and 15% concentrations for extrusion, and 1% for orientation. At these concentrations, the fiber bundle did not remain completely intact.

Dacospin® concentrations of 5, 10 and 25% were evaluated for the extrudate, and a 1% concentration was applied during orientation. At lower concentrations, the fiber bundle was found to separate, but this problem did not persist at the higher concentrations.

Propylene glycol was evaluated at concentrations of 25, 50 and 100%. It could be easily applied to the yarn, however, the fiber bundle tended to separate during orientation even at higher concentrations.

Filapan® performed well during extrusion and orientation steps at a 25% concentration, and imparted good lubricity to the yarn.

Mechanical properties of oriented P4HB yarn produced using a spinneret with 15 holes and PEG400 as spin finish are shown in Table 4.

TABLE 4

Mechanical properties of 15 Filament Oriented P4HB Multifilament Produced with PEG400 as Spin Finish

| Specimen # | # Filaments | Total Denier | Denier per filament (dpf) | Tenacity (gpd) | Break Elongation (%) |
|---|---|---|---|---|---|
| 1 | 15 | 32 | 2.13 | 7.394 | 18.2 |
| 2 | 15 | 32 | 2.13 | 8.081 | 19.6 |
| Average | 15 | 32 | 2.13 | 7.738 | 18.9 |

Mechanical properties of oriented P4HB yarn produced using a spinneret with 30 holes and PEG400 as spin finish are shown in Table 5.

TABLE 5

Mechanical properties of 30 Filament Oriented P4HB Multifilament Produced with PEG400 as Spin Finish

| Specimen # | # Filaments | Total Denier | Denier per filament (dpf) | Tenacity (gpd) | Break Elongation (%) |
|---|---|---|---|---|---|
| 1 | 30 | 68 | 2.27 | 7.232 | 20.4 |
| 2 | 30 | 68 | 2.27 | 7.569 | 16.0 |
| 3 | 30 | 68 | 2.27 | 7.617 | 18.8 |
| Average | 30 | 68 | 2.27 | 7.473 | 18.4 |

Mechanical properties of oriented P4HB yarn produced using a spinneret with 60 holes and PEG400 as spin finish are shown in Table 6.

TABLE 6

Mechanical properties of 60 Filament Oriented P4HB Multifilament Produced with PEG400 as Spin Finish

| Specimen # | # Filaments | Total Denier | Denier per filament (dpf) | Tenacity (gpd) | Break Elongation (%) |
|---|---|---|---|---|---|
| 1 | 60 | 119 | 1.98 | 6.725 | 24.5 |
| 2 | 60 | 119 | 1.98 | 6.619 | 24.0 |
| 3 | 60 | 119 | 1.98 | 6.524 | 25.5 |
| Average | 60 | 119 | 1.98 | 6.622 | 24.7 |

Example 2

Preparation of Multifilament P4HB Braided Sutures and Knitted Tubes

Oriented 60-filament yarns produced according to Example 1 with the following spin finishes were processed into P4HB braided sutures: Tween® 20, PEG400, PEG Stearate, and Dacospin®. The mechanical properties of the braids produced are shown in Table 7.

TABLE 7

Mechanical properties of P4HB braided sutures produced with different spin finishes

| Lot # | Spin Finish | Avg. Diameter (nm) | Denier | Load (kfg) |
|---|---|---|---|---|
| 09X0505-5 | 50% Tween | 0.722 | 5737.3 | 21.0 |
| 09X0513-4 | 50% PEG 400 | 0.671 | 5328.7 | 22.0 |
| 09X0513-7 | 15% PEG Stearate | 0.781 | 5047.4 | 21.3 |
| 09X0519-2 | 5% Dacospin | 0.727 | 5021.7 | 20.8 |

| Lot # | Tenacity (gpd) | Strength (kfg/mm$^2$) | Break Elong. (%) |
|---|---|---|---|
| 09X0505-5 | 3.66 | 3.21 | 40.5 |
| 09X0513-4 | 4.13 | 3.89 | 40.3 |
| 09X0513-7 | 4.22 | 2.78 | 42.2 |
| 09X0519-2 | 4.14 | 3.13 | 42.8 |

Oriented 60-filament yarn produced according to Example 1 with the following spin finishes were also processed into P4HB circular knitted tubes using a single feed, circular weft knitting machine (Lamb Knitting Co., model ST3A/ZA): Tween 20, PEG400, PEG40 Stearate, Dacospin, and Filapan. The width of the flat tube was approximately 9 mm.

Various additional P4HB braid configurations produced using PEG400 were also prepared as indicated in Table 8, and characterized.

TABLE 8

Mechanical properties of various P4HB braid configurations prepared using PEG400

| Example # | # Carriers | TPI | PPI | # Core | Avg. Diameter |
|---|---|---|---|---|---|
| 1 | 16 | 2 | 45 | 5 multi | 0.566 |
| 2 | 16 | 2 | 45 | 6 multi | 0.559 |
| 3 | 2 ply 16 | 2 | N/A | 3 multi | 0.808 |
| 4 | 16 | 2 | 30 | 3 multi | 0.417 |
| 5 | 16 | 2 | 40 | 3 multi | 0.504 |
| 6 | 16 | 2 | 50 | 3 multi | .0495 |
| 7 | 16 | 2 | 60 | 3 multi | 0.563 |
| 8 | 16 | 2 | 75 | 3 multi | 0.577 |
| 9 | 8 | 2 | 75 | 1 multi | 0.405 |
| 10 | 16 | 2 | 75 | 3 multi | 0.587 |
| 11 | 8 | 2 | 75 | 1 multi | 0.412 |
| 12 | 16 | 2 | N/A | 12 multi | 0.712 |
| 13 | 16 | 2 | 70 | 16 multi | 0.742 |
| 14 | 2 ply 12 | 2 | 70 | 5 multi | N/A |

| Example # | Denier | Load (kfg) | Tenacity (gpd) | Break Elong. (%) |
|---|---|---|---|---|
| 1 | 3065 | 16.519 | 5.39 | 38.9 |
| 2 | 2883 | 16.262 | 5.64 | 38.4 |
| 3 | 5328.7 | 22.00 | 4.13 | 40.3 |
| 4 | 2462 | 14.83 | 6.02 | 32.7 |
| 5 | 2520 | 14.341 | 5.69 | 34.9 |
| 6 | 2605 | 14.226 | 5.46 | 39.8 |

TABLE 8-continued

Mechanical properties of various P4HB braid configurations prepared using PEG400

| | | | | |
|---|---|---|---|---|
| 7 | 2608 | 13.50 | 5.18 | 40.9 |
| 8 | 3042 | 12.58 | 4.14 | 39.2 |
| 9 | 1527 | 4.86 | 3.18 | 42.8 |
| 10 | 2699 | 12.00 | 4.45 | 42.5 |
| 11 | 1349 | 4.52 | 3.35 | 50.6 |
| 12 | N/A | 17.045 | N/A | 50.9 |
| 13 | N/A | 19.185 | N/A | 53.6 |
| 14 | N/A | 16.11 | N/A | 46 |

All multifilament used is 120 denier.

Example 3

Scouring of P4HB Multifilament

P4HB knitted circular tubes prepared as described in Example 2 were scoured for 24 hours with 70% aqueous ethanol. All scouring was done at 37° C. in a shaker (50 rpm) in 50 mL plastic Falcon® tubes containing 50 mL of wash solution. Following this treatment, the scoured P4HB knitted tubes (2 gram samples) were tested for cytotoxicity according to the protocol described in Example 4.

Example 4

Cytotoxicity Testing of P4HB Multifilament after Scouring

To test the cytotoxicity of the spin finishes, twice the amount of spin finish residue present on the circular knitted tube after 24 hour washing with 70% ethanol (see Example 3) was determined (by GC for Dacospin®, Tween 20, and PEG20 Stearate, and by GPC-HPLC for PEG400) and supplied in a vial for testing (based on a 2 g sample mass of tube). The amounts used for preparing the cytotoxicity samples are shown in Table 9.

Cytotoxicity testing was undertaken using the ISO Elution Method (1×MEM Extract) following the guidelines of the International Organization for Standardization 10993: Biological Evaluation of Medical Devices, Part 5: Tests for Cytotoxicity: in vitro Methods.

TABLE 9

Results of cytotoxicity testing of Spin Finishes

| Spin Finish | Scour Results Wt % | 2X Residual Wt % | Wt Ratio | Mass Residual mg | Cytotoxicity Result |
|---|---|---|---|---|---|
| Tween ® 20 | 0.60 | 1.20 | 0.012 | 24 | Fail |
| PEG40Stearate | 0.12 | 0.24 | 0.0024 | 4.8 | Fail |
| PEG400 | 0.30 | 0.60 | 0.006 | 12 | Pass |
| DacoSpin ® | 0.07 | 0.14 | 0.0014 | 2.8 | Fail |

Additionally, 2 g of the knitted tube itself after 10 minute ethanol washing, was submitted for cytotoxicity testing. Results for the washed, knitted tubes are shown in Table 10.

TABLE 10

Results for cytotoxicity testing of 2 g of P4HB multifilament after 10 minute ethanol wash*.

| Spin Finish | Residual Wt % | Wt Ratio | Calculated Residual Mass (mg) | Cytotoxicity Result |
|---|---|---|---|---|
| Tween ® 20 | 1.65 | 0.017 | 33 | Fail |
| PEG40Stearate | 0.52 | 0.005 | 10.4 | Pass |
| PEG400 | 0.77 | 0.008 | 15.4 | Pass |
| DacoSpin ® | 0.67 | 0.007 | 13.4 | Fail |

*The Filapan spin finish coated on the knitted tube also failed this cytotoxicity test As shown in Table 10, only the PEG400 spin finish passed the cytotoxicity testing at twice the level present after 24 hours of ethanol washing, and as a residue on an actual knitted sample of P4HB multifilament after a 10 minute ethanol wash. PEG40 Stearate passed cytotoxicity testing as a residue on the washed mesh, but both Tween® 20 and Dacospin® failed both of these cytotoxicity tests.

Example 5

Braided P4HB Suture Comprising an Outer Multifilament Sheath and an Inner P4HB Monofilament Core P4HB multifilament fiber (120 denier), comprising two 60-filament yarns produced as described in Example 1, was placed on 16 carrier bobbins. A size 1 P4HB monofilament fiber (produced as described by the method in Example 7) was fed into the braider core eyelet and run at 70 picks per inch (PPI) to produce a P4HB braided suture comprising an outer multifilament sheath of P4HB, and an inner P4HB monofilament core with the properties described in Table 11.

TABLE 11

Properties of a braided P4HB suture with an outer multifilament sheath and an inner P4HB monofilament core

| Example # | # Carriers | TPI | PPI | # Core | Avg. Diameter |
|---|---|---|---|---|---|
| 1 | 16 | 2 | 70 | 1 mono size 1 | 0.743 |

| Example # | Denier | Load (kfg) | Tenacity (gpd) | Break Elong. (%) |
|---|---|---|---|---|
| 1 | N/A | 26.654 | N/A | 46.4 |

All multifilament used is 120 denier.

Example 6

Braided P4HB Suture Comprising an Outer Multifilament and Monofilament Sheath and an Inner P4HB Monofilament Core P4HB multifilament fiber (120 denier), produced as described in Example 1, was placed on 8 of 16 carrier bobbins. The remaining 8 bobbins were filled with size 5/0 P4HB monofilament fiber (produced as described by the method in Example 7). A bundle of 3 ply size 5/0 P4HB monofilament fiber was fed into the braider core eyelet, and run at 70 picks per inch to produce a P4HB braided suture comprising an outer multifilament and monofilament sheath of P4HB, and an inner P4HB monofilament 3-ply core with the properties described in Table 12.

TABLE 12

Properties of a braided P4HB suture with an outer multifilament sheath and an inner P4HB monofilament core

| Example # | # Mono Carriers | # Multi Carriers | TPI | PPI | # Core |
|---|---|---|---|---|---|
| 1 | 8 mono size 5/0 | 8 multi | 2 | 70 | 3 ply size 5/0 mono |

| Example # | Avg. Diameter | Denier | Load (kfg) | Tenacity (gpd) |
|---|---|---|---|---|
| 1 | N/A | N/A | N/A | N/A |

All multifilament used is 120 denier.

Example 7

Preparation of P4HB Monofilament by Melt Extrusion

Bulk P4HB resin in pellet form was dried to under 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight hole spinneret assembly. Processing profile ranges from 40° C. to 260° C. for temperatures, and 400 psi to 2000 psi for pressures, were used. The molten filaments were water quenched and conveyed into a three-stage orientation, with inline relaxation, before winding of the monofilaments on spools. Test values for extruded monofilament fiber are shown in Table 13.

TABLE 13

Mechanical Test Data for P4HB Monofilament Fiber

| Fiber USP Size | Diameter, mm | Breaking Strength, Kg | Break Elongation |
|---|---|---|---|
| 5/0 | 0.150 | 1.80 | 30% |
| 6/0 | 0.100 | 1.00 | 29% |

Example 8

Preparation of a P4HB Monofilament Mesh with Tween® 20

Spools with P4HB monofilament fiber prepared as described in Example 7 were converted into Tween® 20 coated P4HB monofilament mesh as follows: Monofilament fibers from 49 spools were pulled under uniform tension to the surface of a warp beam. A warp is a large wide spool onto which individual fibers are wound in parallel to provide a sheet of fibers ready for coating with a 10% solution of Tween® 20 lubricant. Tween® 20 lubricant was added to the surface of the sheet of fiber by means of a 'kiss' roller that was spinning and was immersed in a bath filled with Tween® 20. The upper surface of the roller was brought into contact with the sheet of fiber, and the roller spun at a uniform speed to provide a consistent application of Tween® 20 finish. Following the application of Tween® 20, the sheet of fiber was placed onto a creel position such that each spooled fiber was aligned and wrapped side by side to the next spooled fiber on a warp beam. Next, warp beams were converted into a finished mesh fabric by means of interlocking knit loops. Eight warp beams were mounted in parallel onto a tricot machine let-offs and fed into the knitting elements at a constant rate determined by the 'runner length'. Each individual monofilament fiber from each beam was fed through a series of dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll ready for finished product inspection.

Example 9

Scouring of P4HB Monofilament Mesh and Cytotoxicity Testing

The P4HB monofilament mesh produced according to the method of Example 8 was scored ultrasonically with water, heat set in hot water, and then washed with a 70% aqueous ethanol solution. Cytotoxicity testing of two grams of the mesh was undertaken using the ISO Elution Method (1×MEM Extract) following the guidelines of the International Organization for Standardization 10993: Biological Evaluation of Medical Devices, Part 5: Tests for Cytotoxicity: in vitro Methods. The scoured P4HB monofilament mesh passed the cytotoxicity testing. The content of Tween 20 prior to scouring was approximately 0.3 wt %, and at this level the mesh failed the cytotoxicity testing. The residual content of Tween 20 after scouring was approximately 0.03 wt %, and at this level the mesh passed the cytotoxicity testing.

Example 10

Coating of P4HB Braided Sutures with Spin Finish

Braided P4HB sutures prepared according to Example 2, and scoured by the method of Example 3, can be recoated with PEG400. Cytotoxicity testing of a braided P4HB suture coated with approximately 6 wt % PEG400 was undertaken using the ISO Elution Method (1×MEM Extract) following the guidelines of the International Organization for Standardization 10993: Biological Evaluation of Medical Devices, Part 5: Tests for Cytotoxicity: in vitro Methods. The PEG400 braided suture passed the cytotoxicity testing at this coating weight.

Example 11

Preparation of Hybrid P4HB/Polypropylene Meshes

Spools with P4HB monofilament fiber prepared as described in Example 7 were converted into Tween® 20 coated P4HB monofilament mesh as follows. Monofilament fibers from 49 spools were pulled under uniform tension to the surface of a warp beam. A warp is a large wide spool onto which individual fibers are wound in parallel to provide a sheet of fibers ready for coating with a 10% solution of Tween® 20 lubricant. Tween® 20 lubricant was added to the surface of the sheet of fiber by means of a 'kiss' roller that was spinning and was immersed in a bath filled with Tween® 20. The upper surface of the roller was brought into contact with the sheet of fiber, and the roller spun at a uniform speed to provide a consistent application of Tween® 20 finish. Following the application of Tween® 20, the sheet of P4HB fibers was placed onto a creel position such that each spooled fiber was aligned and wrapped side by side to the next spooled fiber to form a set of P4HB warp beams. Similarly 49 spools of polypropylene monofilament, with diameter similar to P4HB monofilament, were processed to form a set of polypropylene warp beams. Next, warp beams were converted into a finished mesh fabric by means of interlocking knit loops. Each set of warp beams was mounted in parallel onto a tricot machine on two separate let-offs and each set of beams was threaded into a separate guide bar for feeding into the knitting needles. The P4HB warp beam fiber was fed to the front guide bar and the polypropylene warp beam fiber was fed to the back guide bar. Each individual monofilament fiber from each beam was fed through a series of dynamic tension elements down into the knitting 'guides'. The guide bars directed the fibers around the needles forming the mesh fabric structure. Knitting patterns were selected so that intact polypropylene knits would remain once the absorbable P4HB monofilament was degraded from the construction in vivo. Both materials (P4HB and polypropylene) were knitted together to form one knitted construction. The mesh fabric was then pulled off the needles by the take down rollers at a constant rate of speed determined by the fabric 'quality'. The hybrid mesh fabric was then taken up and wound onto a roll.

The P4HB filaments were then dissolved away by immersing the hybrid mesh in chloroform. Examples of hybrid meshes prepared with two different sizes of monofilament, and two ratios of polypropylene (PP) to P4HB are listed in Table 14.

TABLE 14

Hybrid Mesh Prepared from Polypropylene (PP) and P4HB

| Identification | Mesh Description |
|---|---|
| SN 3528 | 75% PP, 25% P4HB; Tepha Lot # 902001; filament diameter—100 μm |
| SN 3566 | 75% PP, 25% P4HB; Tepha Lot # 902003; filament diameter—150 μm |
| SN 3529 | 50% PP, 50% P4HB; Tepha Lot # 902002; filament diameter—100 μm |
| SN 3567 | 50% PP, 50% P4HB; Tepha Lot # 902004; filament diameter—150 μm |

To demonstrate that the hybrid meshes listed in Table 14 would progressively lose burst strength after implantation in vivo, samples of each mesh (n=5 for each time point, 2 inch×2 inch squares) were placed in 3M HCl at 37° C. for 5, 24 and 48 hours prior to being subjected to mesh burst strength testing. Mesh Burst testing was performed at the required time points according to ASTM D6797-02 (Standard Test Method for Bursting Strength of Fabrics Constant-Rate-of-Extension (CRE) Ball Burst Test) at ambient conditions. The ball burst fixture had a 1.6 cm circular opening and a 1 cm diameter half-rounded probe. Molecular weight measurements were made by placing hybrid mesh in chloroform to dissolve P4HB filament, and then determining molecular weights (Mw) by GPC. Over the course of the study, it became evident which filaments within the mesh were P4HB and which were polypropylene. By the 48 hr time point, the P4HB filaments were opaque white in color, and many were crumbling from the mesh. The polypropylene filaments did not appear to change over time. Test data for the samples shown in Table 14 at each time point, including time t=0, is shown in Tables 15-18.

TABLE 15

Burst Strength and Mw testing data for SN 3528 Hybrid Mesh samples - In Vitro testing

| Incubation Time (hr) | Avg. thick (mm) | Thickness Std Dev | Peak Load (KgF) | Peak Load Std Dev |
|---|---|---|---|---|
| 0 | 0.374 | 0.021 | 5.933 | 0.727 |
| 5 | 0.339 | 0.014 | 5.277 | 0.431 |
| 24 | 0.355 | 0.032 | 5.263 | 0.954 |
| 48 | 0.326 | 0.007 | 6.025 | 0.576 |

| Incubation Time (hr) | Extension at Peak Load (mm) | Extension at Peak Load Std Dev | % Strength Retention | Mw (Da) | % Mw Retention |
|---|---|---|---|---|---|
| 0 | 5.967 | 0.236 | 100 | 266,830 | 100.0 |
| 5 | 6.875 | 0.362 | 88.9 | 209,900 | 78.7 |
| 24 | 6.556 | 0.382 | 88.7 | 111,480 | 41.8 |
| 48 | 5.363 | 0.545 | 101.6 | 64,816 | 24.3 |

TABLE 16

Burst Strength and Mw testing data for SN 3566 Hybrid Mesh samples - In Vitro testing

| Incubation Time (hr) | Avg. thick (mm) | Thickness Std Dev | Peak Load (KgF) | Peak Load Std Dev |
|---|---|---|---|---|
| 0 | 0.863 | 0.011 | 14.319 | 1.139 |
| 5 | 0.861 | 0.012 | 10.465 | 1.211 |
| 24 | 0.870 | 0.008 | 10.684 | 1.214 |
| 48 | 0.860 | 0.012 | 11.648 | 1.163 |

| Incubation Time (hr) | Extension at Peak Load (mm) | Extension at Peak Load Std Dev | % Strength Retention | Mw (Da) | % Mw Retention |
|---|---|---|---|---|---|
| 0 | 8.142 | 0.274 | 100 | 310,260 | 100.0 |
| 5 | 9.634 | 0.653 | 73.1 | 245,390 | 79.1 |
| 24 | 10.283 | 0.419 | 74.6 | 127,270 | 41.0 |
| 48 | 10.516 | 0.501 | 81.3 | 73,388 | 23.7 |

TABLE 17

Burst Strength and Mw testing data for SN 3529 Hybrid Mesh samples - In Vitro testing

| Incubation Time (hr) | Avg. thickness (mm) | Thickness Std Dev | Peak Load (KgF) | Peak Load Std Dev |
|---|---|---|---|---|
| 0 | 0.485 | 0.018 | 11.443 | 0.553 |
| 5 | 0.456 | 0.010 | 8.940 | 0.574 |
| 24 | 0.472 | 0.023 | 7.380 | 0.886 |
| 48 | 0.462 | 0.018 | 7.704 | 1.045 |

| Incubation Time (hr) | Extension at Peak Load (mm) | Extension at Peak Load Std Dev | % Strength Retention | Mw (Da) | % Mw Retention |
|---|---|---|---|---|---|
| 0 | 5.563 | 0.286 | 100 | 256,990 | 100.0 |
| 5 | 4.983 | 0.128 | 78.1 | 207,520 | 80.8 |
| 24 | 5.256 | 0.354 | 64.5 | 114,390 | 44.5 |
| 48 | 5.698 | 0.363 | 67.3 | 71,319 | 27.8 |

Example 12

Preparation of a Collagen Coated PHA Device

A monofilament P4HB mesh prepared as described in Example 8 can be coated with collagen by immersion into an aqueous slurry of 2% bovine skin collagen (prepared according to Example 1 of U.S. Pat. No. 5,108,424 to Hoffman et al). The slurry includes 8% glycerol and 17% ethanol. The coated mesh is removed from the slurry, and allowed to dry for approximately 30 mins at room temperature. The coating and drying steps are repeated three more times to yield a collagen coated P4HB monofilament mesh.

TABLE 18

Burst Strength and Mw testing data for SN 3567 Hybrid Mesh samples - In Vitro testing

| Incubation Time (hr) | Avg. thick (mm) | Thickness Std Dev | Peak Load (KgF) | Peak Load Std Dev |
|---|---|---|---|---|
| 0 | 0.768 | 0.032 | 32.428 | 3.110 |
| 5 | 0.817 | 0.018 | 23.954 | 1.217 |
| 24 | 0.814 | 0.009 | 15.621 | 1.591 |
| 48 | 0.820 | 0.014 | 16.498 | 1.842 |

| Incubation Time (hr) | Extension at Peak Load (mm) | Extension at Peak Load Std Dev | % Strength Retention | Mw (Da) | % Mw Retention |
|---|---|---|---|---|---|
| 0 | 8.747 | 0.708 | 100 | 302,670 | 100.0 |
| 5 | 7.665 | 0.122 | 73.9 | 235,550 | 77.8 |
| 24 | 7.484 | 0.297 | 48.2 | 120,880 | 39.9 |
| 48 | 8.194 | 0.487 | 50.9 | 77,384 | 25.6 |

Example 13

Crosslinking of a Collagen Coated PHA Monofilament Mesh

The coated mesh prepared in Example 12 can be crosslinked by exposure to formaldehyde vapor for five minutes. The resulting composite is then allowed to dry for approximately 15 mins in air at room temperature, and is then vacuum dried to remove residual crosslinking agent and any moisture.

Example 14

Tissue Drag of Scoured TephaFLEX Braid

A 16-carrier, single-ply braided suture over a 6-ply core was prepared from 60-filament TephaFLEX yarn using PEG400 as a spin finish. The braid was then scoured in water for various lengths of time to remove the PEG400.

The amount of force required to pull the suture through tissue was determined using a tissue drag test. In this test, the suture is passed through a simulated tissue multiple times, and one of the free ends is fixed to the movable grip of a universal testing machine. The simulated tissue is held stationary in a frame below the movable cross member. The test is initiated and the kilograms of force (Kgf) required to pull the suture through the simulated tissue is recorded. The suture may be tested dry or after wetting in water. Results for the 16-carrier over 6-ply core braided TephaFLEX suture are show in Table 19. Comparison is made to a Vicryl control suture. As can be seen in Table 19, the 10-minute scoured TephaFLEX braid compares well to the Vicryl braid in that the drag forces are similar. However, as the time of scouring increases, and the amount of residual PEG400 decreases, the drag force increases.

TABLE 19

Drag force measurements for TephaFLEX braid.

| Sample Description | Avg Drag Force (Kgf) | Peak Load (Kgf) |
|---|---|---|
| Vicryl Size 2 Lot # CDM945, wet | 0.338 | 0.358 |
| TephaFLEX Lot # 100136 Size 2, 10 min scoured sterile, wet | 0.323 | 0.373 |
| TephaFLEX Lot # 100198 Size 2, 2 hours scoured sterile, wet | 0.415 | 0.475 |

Example 15

Tissue Drag of PEG2000 Coated TephaFLEX Braids

A 15-minute scoured TephaFLEX braid of Example 14 was coated with a PEG2000 coating to reduce the amount of tissue drag. PEG2000 was dissolved in ethanol (30% wt./vol.) and the braided suture was pulled through a bead of the solution to thoroughly wet the braid. The braid was allowed to dry to leave behind a residue of PEG2000 at a coating weight of approximately 7% by wt. The tissue drag of the coated suture after wetting in water was performed as described in Example 14, and the results are shown in Table 20.

TABLE 20

Drag force measurements for TephaFLEX braid coated with PEG2000 compared to Vicryl and uncoated TephaFLEX controls.

| Specimen Name | Avg Drag Force (kgf) | Peak Load (kgf) | Avg Drag Force, Relative to Vicryl (%) | Peak Load, Relative to Vicryl (%) |
|---|---|---|---|---|
| Vicryl Control | 0.319 | 0.344 | N/A | N/A |
| Scoured TephaFLEX Control | 0.284 | 0.299 | 89% | 87% |
| PEG2000 Coated TephaFLEX Braid | 0.242 | 0.288 | 76% | 84% |

As can be seen in the table, the drag force of the coated suture is lower than that of the uncoated TephaFLEX and Vicryl controls, thus demonstrating that the PEG2000 coating is effective at reducing the tissue drag of the braided suture.

Example 16

Tissue Drag of PVA Coated TephaFLEX Braids

A 15-minute scoured TephaFLEX braid of example 14 was coated with a polyvinyl alcohol (PVA) coating to reduce the amount of tissue drag. PVA was dissolved in water at 8% and the braided suture was pulled through a bead of the solution to thoroughly wet the braid. The braid was allowed to dry to leave behind a residue of PVA at a coating weight of approximately 3% by wt. The tissue drag of the coated suture after wetting in water was performed as described in Example 14, and the results are shown in Table 21. As can be seen in the table, the drag force of the PVA-coated suture is substantially lower than that of the uncoated TephaFLEX and Vicryl controls, thus demonstrating that the PVA coating is effective at reducing the tissue drag of the braided suture.

TABLE 21

Drag force measurements for TephaFLEX braid coated with PVA compared to Vicryl and uncoated TephaFLEX controls.

| Specimen Name | Avg Drag Force (kgf) | Peak Load (kgf) | Relative to Vicryl Avg Drag Force (%) | Relative to Vicryl Peak Load (%) |
|---|---|---|---|---|
| Vicryl Control | 0.316 | 0.337 | N/A | N/A |
| Scoured TephaFLEX Control | 0.305 | 0.346 | 97% | 103% |
| PVA Coated TephaFLEX Braid | 0.173 | 0.202 | 55% | 60% |

Modifications and variations of the invention described herein will be obvious to those skilled in the art and are intended to come within the scope of the appended claims.

We claim:

1. A medical device comprising a polymeric multifilament yarn,
wherein the polymer consists of a polyhydroxyalkanoate, wherein the denier per filament is less than 4.0, and the multifilament yarn has a tenacity greater than 6.1 grams per denier.

2. The device of claim 1, wherein the device is selected from the group consisting of barbed sutures, braided sutures, ligatures, hybrid sutures of monofilament and multifilament fibers, braids, knitted or woven meshes, monofilament meshes, multifilament meshes, knitted tubes, stents, stent grafts, drug delivery devices, devices for temporary wound or tissue support, devices for soft tissue repair, devices for replacement or regeneration, repair patches, tissue engineering scaffolds, retention membranes, anti-adhesion membranes, tissue separation membranes, hernia repair devices, breast reconstruction devices, devices for blepharoplasty, devices for facial scar revisions, devices for forehead lifts, devices for mentoplasty, devices for malar augmentation, devices for otoplasty, devices for rhinoplasty, devices for neck lift surgery, devices for rhytidectomy, threadlift devices to lift and support sagging areas of the face, brow, and neck, fixation devices, cardiovascular patches, vascular closure devices, vascular grafts, slings, biocompatible coatings, rotator cuff repair devices, meniscus repair devices, adhesion barriers, guided tissue repair/regeneration devices, articular cartilage repair devices, nerve guides, tendon repair devices, ligament repair devices, intracardiac septal defect repair devices, left atrial appendage (LAA) closure devices, pericardial patches, bulking and filling agents, vein valves, heart valves, bone marrow scaffolds, meniscus regeneration devices, ligament and tendon graft, ocular cell implants, spinal fusion devices, imaging devices, skin substitutes, dural substitutes, bone graft substitutes, wound dressings, and hemostats.

3. The device of claim 2, wherein the breast reconstruction device is selected from the group consisting of devices for breast augmentation, devices for mastopexy, devices for breast reduction, devices for breast positioning and shaping, and devices for breast reconstruction following mastectomy.

4. The device of claim 2, comprising a braided suture wherein the suture comprises an outer polyhydroxyalkanoate multifilament sheath and an inner polyhydroxyalkanoate monofilament core.

5. The device of claim 4, comprising a suture wherein the suture comprises an outer polyhydroxyalkanoate multifilament and monofilament sheath, and an inner polyhydroxyalkanoate monofilament core.

6. The device of claim 4, wherein the polyhydroxyalkanoate comprises 4-hydroxybutyrate.

7. The device of claim 4, wherein the inner monofilament core is barbed, or is made from a non-degradable polymer.

8. The device of claim 1, wherein the device comprises one or more additional components selected from the group consisting of plasticizers, nucleants, collagen, crosslinked collagen, blends or copolymers of polyhydroxyalkanoates, blends or copolymers of lactic acid, glycolic acid, caprolactone, p-dioxanone, or trimethylene carbonate, polymer additives, dyes, compatibilizers, fillers, therapeutic agents, diagnostic agents, and prophylactic agents.

9. The device of claim 1, wherein the device is a suture and contains at least one or more fibers with contrasting dye to provide an identifiable color trace in the suture strand.

10. The device of claim 1, wherein the device is a suture used for ligament and tendon repair.

11. The device of claim 1, wherein the device is a surgical mesh.

12. The device of claim 11, wherein the surgical mesh comprises polyhydroxyalkanoate fiber and a permanent fiber.

13. The device of claim 12, wherein the permanent fiber is polypropylene, a polyester, or a combination thereof.

14. The device of claim 11, wherein the surgical mesh comprises monofilament fibers.

15. The device of claim 11, wherein the surgical mesh has been coated or encapsulated with collagen.

16. The device of claim 15, wherein the porosity of the collagen is at least 5 μm in diameter.

17. The device of claim 15, wherein the polyhydroxyalkanoate component is, coated or encapsulated with collagen, the collagen is crosslinked, and the device is sterilized with ethylene oxide or by irradiation.

18. A method comprising implanting or administering a medical device at a site in or on a patient in need thereof,
wherein the medical device comprises a polymeric multifilament yarn,
wherein the polymer consists of a polyhydroxyalkanoate, and
wherein the denier per filament is less than 4.0 and the multifilament yarn has a tenacity greater than 6.1 grams per denier and
wherein the medical device is selected from the group consisting of barbed sutures, braided sutures, ligatures, hybrid sutures of monofilament and multifilament fibers, braids, knitted or woven meshes, monofilament meshes, multifilament meshes, knitted tubes, stents, stent grafts, drug delivery devices, devices for temporary wound or tissue support, devices for soft tissue repair, devices for replacement or regeneration, repair patches, tissue engineering scaffolds, retention membranes, anti-adhesion membranes, tissue separation membranes, hernia repair devices, breast reconstruction devices, devices for blepharoplasty, devices for facial scar revisions, devices for forehead lifts, devices for mentoplasty, devices for malar augmentation, devices for otoplasty, devices for rhinoplasty, devices for neck lift surgery, devices for rhytidectomy, threadlift devices to lift and support sagging areas of the face, brow, and neck, fixation devices, cardiovascular patches, vascular closure devices, vascular grafts, slings, biocompatible coatings, rotator cuff repair devices, meniscus repair devices, adhesion barriers, guided tissue repair/regeneration devices, articular cartilage repair devices, nerve guides, tendon repair devices, ligament repair devices, intracardiac septal defect repair devices, left atrial appendage (LAA) closure devices, pericardial patches, bulking and filling agents, vein valves, heart valves, bone marrow scaffolds, meniscus regeneration devices, ligament and tendon graft, ocular cell implants, spinal fusion devices, imaging devices, skin substitutes, dural substitutes, bone graft substitutes, wound dressings, and hemostats,
  wherein the breast reconstruction device is selected from the group consisting of devices for breast augmentation, devices for mastopexy, devices for breast reduction, devices for breast positioning and shaping, and devices for breast reconstruction following mastectomy.

19. The device of claim 1, wherein the filaments are derived by melt-extrusion processing of the polyhydroxyalkanoate polymer between 40° C. and 275° C., allowing the polymer to cool and solidify and applying polymers or oligomers of ethylene oxide or propylene oxide polyethylene glycol sorbitan monolaurate to the filaments or yarn by passage through a spin finish applicator either inline or offline.

20. The device of claim 19, wherein the multifilament yarn is coated with a coating material selected from the group consisting of polymers or oligomers of ethylene oxide, polymers or oligomers of propylene oxide, polyvinyl alcohol, and combinations thereof.

21. The device of claim 1, wherein the polyhydroxyalkanoate has a molecular weight between 50,000 and 1,200,000 measured by gel permeation chromatography.

22. The device of claim 20, wherein the polyhydroxyalkanoate comprises 4-hydroxybutyrate.

23. The device of claim 20, wherein the coating material is polyethylene glycol having an average molecular weight of 1000 to 10,000 daltons.

24. The device of claim 20, wherein the coating material is polyvinyl alcohol.

25. The device of claim 20, wherein the average tissue drag force of the coated braid is reduced at least 10% relative to the uncoated braid.

26. A medical device comprising an oriented polyhydroxyalkanoate multifilament yarn, wherein the denier per filament is less than 4.0, and the multifilament yarn has a tenacity greater than 6.1 grams per denier.

27. The device of claim 21, wherein the coating material is polyethylene glycol sorbitan monolaurate.

28. The device of claim 19, wherein the polymer is polyethylene glycol having an average molecular weight of 100 to 1000 daltons in a spin finish.

29. The device of claim 17, treated with plasma gas prior to coating or encapsulating with collagen.

* * * * *